United States Patent [19]
Abela

[11] Patent Number: 5,586,982
[45] Date of Patent: * Dec. 24, 1996

[54] CELL TRANSFECTION APPARATUS AND METHOD

[76] Inventor: George S. Abela, 80 Longfellow Rd., Wellesley, Mass. 02181

[*] Notice: The term of this patent shall not extend beyond the expiration date of Pat. No. 5,246,437.

[21] Appl. No.: 276,324

[22] Filed: Jul. 18, 1994

Related U.S. Application Data

[63] Continuation-in-part of Ser. No. 53,206, Apr. 28, 1993, Pat. No. 5,330,467, which is a continuation of Ser. No. 866,473, Apr. 10, 1992, Pat. No. 5,246,437.

[51] Int. Cl.⁶ ................................................. A61B 17/36
[52] U.S. Cl. ............................... 606/28; 606/14; 606/15; 606/29; 604/21
[58] Field of Search ..................... 606/27–30, 41, 606/45, 2, 3, 7, 13–17; 604/21, 22

[56] References Cited

U.S. PATENT DOCUMENTS

| | | |
|---|---|---|
| Re. 31,815 | 1/1985 | Alfano . |
| 4,648,892 | 3/1987 | Kittrell et al. . |
| 4,662,368 | 5/1987 | Hussein et al. ........................... 606/28 |
| 4,686,979 | 8/1987 | Gruen et al. . |
| 4,748,980 | 6/1988 | Cremer et al. . |
| 4,785,806 | 11/1988 | Deckelbaum . |
| 4,785,815 | 11/1988 | Cohen . |
| 4,860,743 | 8/1989 | Abela . |
| 4,913,142 | 4/1990 | Kittrell et al. . |
| 5,019,075 | 5/1991 | Spears et al. ............................ 606/28 |
| 5,041,109 | 8/1991 | Abela . |
| 5,061,265 | 10/1991 | Abela et al. . |
| 5,071,222 | 12/1991 | Laakman et al. ........................ 606/28 |
| 5,190,540 | 3/1993 | Lee ........................................... 606/28 |
| 5,242,438 | 9/1993 | Saadatmanesh . |
| 5,246,437 | 9/1993 | Abela . |
| 5,328,470 | 7/1994 | Nabel et al. ........................... 606/194 |
| 5,330,467 | 7/1994 | Abela . |

FOREIGN PATENT DOCUMENTS

WO93/20762  10/1993  WIPO .

OTHER PUBLICATIONS

Biochemica and Biophysica, Toshiyuki Takai and Hitoshi Ohmori, 1992, pp. 161–165, Enhancement of DNA Transfection Efficiency By Heat Treatment of Cultured Mammalian Cells.

"Development and Early Clinical Applications of a Lateral-Aiming Laser Probe", Daijo Hashimoto, Lasers in Medical Science, vol. 2:25, Sep. 8, 1986, pp. 25–28.

"The Perforated Balloon Catheter: Assessment and Minimization of Arterial Trauma", JACC, vol. 19, No. 3, Mar. 1, 1992, p. 107A Charles Lambert and Timothy Grady.

"High–Velocity Microprojectiles for Delivering Nucleic Acids Into Living Cells", T. M. Klein, E. D. Wolf, R. Wu, & J. C. Sanford, Letters to Nature, vol. 327, May 7, 1987, pp. 70–73.

"Biolistic Transformation: Microbes to Mice", S. A. Johnston, Nature, vol. 346, Aug. 23, 1990, pp. 776–777.

(List continued on next page.)

Primary Examiner—Angela D. Sykes
Assistant Examiner—Michael Peffley
Attorney, Agent, or Firm—William L. Feeney; Kerkam, Stowell, Kondracki & Clarke, P.C.

[57] ABSTRACT

An apparatus and associated method provides for the application of a cell treatment agent, such as genetic material or drugs to be inserted within the cells of a patient in vivo. The apparatus may be a catheter arrangement with various embodiments for applying heat to a patient's cells in vivo in order to improve transfection efficiency or application efficiency. Laser beams may be applied directly to the cells. Alternately, the cells may be heated by electrical heating, chemical heating, radio frequency heating, microwave heating, infrared heating, ultrasound heating, or indirect laser heating. Further, the treatment agent may be heated prior to its application to the patient such that the treatment agent heats the cells of the patient.

34 Claims, 8 Drawing Sheets

OTHER PUBLICATIONS

"Introduction of Foreign Genes Into Tissues of Living Mice by DNA–Coated Microprojectiles", R. Sanders Williams et al, Proc. Natl. Acad. Sci. USA, vol. 88, Apr. 1991, pp. 2726–2730, Genetics.

"Gene Transfer Into Mammalian Cells By Rapid Freezing", Kiyoshi Sasaki et al, In Vitro Cell. Dev. Biol. 27A: pp. 86–88, Jan. 1991.

"High Efficiency Gene Transfection by Electroporation Using a Radio–Frequency Electric Field", Donald C. Chang et al, Biochimica et Biophysica Acta, 1992 (1991) pp. 153–160.

"Site–Specific Gene Expression in Vivo by Direct Gene Transfer Into the Arterial Wall", Elizabeth G. Nabel et al, Science, Sep. 14, 1990, pp. 1285–1288.

"Direct In Vivo Gene Transfer Into the Coronary and Peripheral Vasculatures of the Intact Dog", Chang S. Lim et al, Circulation, vol. 83, No. 6, Jun. 1991, pp. 2007–2011.

"Direct Gene Transfer Into Human Cultured Cells Facilitated by Laser Micropuncture of the Cell Membrane", Wen Tao et al, Proc. Natl. Acam. Sci. USA, vol. 84, pp. 4180–4184, Jun. 1987.

"The Laser Method for Efficient Introduction of Foreign DNA Into Cultured Cells", Shun–ichi Kurata et al, Experimental Cell Research 162, (1986), pp. 372–378.

CELL TRANSFECTION APPARATUS AND METHOD

CROSS-REFERENCE TO RELATED APPLICATIONS

This application is a continuation-in-part of U.S. Ser. No. 08/053,206 filed Apr. 28, 1993, now U.S. Pat. No. 5,330,467 which in turn was a continuation of Ser. No. 07/866,473 filed Apr. 10, 1992, now U.S. Pat. No. 5,246,437 issued Sep. 11, 1993. Both of those prior applications were filed in the name of the present inventor and entitled "Cell Treatment Method And Apparatus" and both are hereby incorporated by reference.

BACKGROUND OF THE INVENTION

This invention relates to a cell treatment apparatus and method. More specifically, this invention relates to a treatment apparatus and method for transfecting a patient's cells in vivo.

Various techniques have been used, at least experimentally, for transfection of cells (i.e., insertion of new genetic material into the DNA structure of cells).

One technique for transfection of cells has used laser poration. This approach has been performed in vitro using a laser beam to porate a single cell at a time under a specially adapted microscope. The microscope allows the direct puncture of the cell membrane in the presence of the gene. Specifically, an operator directs the laser beam towards an individual cell and the puncture of the cell membrane allows genetic material on the same side as the cell to enter into the cell. This approach is labor intensive and not practical to use in vivo. This laser poration technique is described in the article by Tao et al. entitled "Direct Gene Transfer Into Human Cultured Cells Facilitated By Laser Micropuncture of Cell Membrane" in the Proceedings of the National Academy of Science in 1987; 84:4180–4184.

Other approaches to transfection of cells have included chemical methods or electrical poration used in a cell culture, but such methods have not been readily applicable in vivo. In other words, such methods may allow treatment of cells which have been removed from the patient, but do not allow treatment of cells remaining with the patient (human or animal).

The Nabel et al. article entitled "Site-Specific Gene Expression in Vivo by Direct Gene Transfer Into the Arterial Wall" in Science in 1990; 249(4974):1285–1288 discloses a technique for transfecting genes in vivo which has been used in the arteries of pigs. This technique uses a catheter with a dual balloon system at the tip of the catheter. The two balloons are inflated to create a temporary chamber which allows the exposure of the arterial wall to a viral transporting agent in solution. This has been used successfully to transfect the arterial wall with a DNA-plasmid having a viral carrier. However, this double balloon method requires 30 minutes to bathe the arterial wall with the DNA-plasmid to be effective. This is not feasible in certain applications such as in the coronary circulation. Moreover, the time required for such a technique to work may pose severe problems even at other locations within the arteries of an animal or human.

The Lim et al. article entitled "Direct In Vivo Gene Transfer Into the Coronary and Peripheral Vasculatures of the Intact Dog" appearing in Circulation, volume 83, no. 6, June 1991, pages 2007–2011, discloses a technique where endothelial cells are removed from the test animal and then transfected prior to reintroduction into the animal. In addition to that in vitro technique, the article describes in vivo transfection of arteries of dogs using catheters placed in peripheral vessels of the dogs. Proximal and distal lumens of the vessels were occluded with removable ligatures. In somewhat similar fashion to the dual balloon system, a temporary chamber is established and a transfection solution is supplied into that temporary chamber within the vessels of the animal. The article describes allowing the transfection solution to remain in the vessel for one hour.

In the two above incorporated by reference applications, the present inventor has disclosed cell treatment (more specifically cell transfection) of a patient's cells in vivo by use of a laser catheter. No admission is made or intended that these prior applications of the present inventor are necessarily prior art to the present application. However, it is noted that the present inventor has discovered the use of various additional techniques for in vivo transfection of a patient's cells. As used herein, in vivo shall refer to treatment of a patient's cells without removing the cells from the patient. Thus, in vivo treatment involves treatment of cells within or on the patient.

OBJECTS AND SUMMARY OF THE INVENTION

Accordingly, it is a primary object of the present invention to provide a new and improved cell transfection apparatus and method.

A more specific object of the present invention is to provide for highly efficient cell transfection in vivo.

A further object of the present invention is to provide for transfection of cells in vivo relatively quickly (i.e., the cells in vivo need not be exposed for such long periods that lengthy disruptions, such as blocking of artery flow, are required).

The above and other objects which will become more apparent as the description proceeds are realized by an apparatus for cell transfection including an instrument with a housing having a wall with at least one hole therein. A heater is operatively connected to the instrument so as to apply heat to cells of a patient in vivo. A source of treatment agent including a DNA plasmid is operatively connected to the instrument so as to apply treatment agent to the heated cells by way of a treatment channel inside the instrument and extending to the hole. The treatment agent is operable to transfect the heated cells.

The heater, which may also be called a heating means, may be realized by various alternate constructions. In a first embodiment, the heater includes an optical fiber within the instrument for applying laser energy by way of the hole to heat the cells. In a second embodiment, the heater includes an optical fiber within the instrument for heating an opaque portion of the instrument such that the opaque portion in turn heats the cells. In a third embodiment, the heater is an RF source which heats the cells by application of radio frequency energy. In a fourth embodiment, the heater is a microwave source which heats the cells by application of microwave energy. In a fifth embodiment, the heater is an electrical heater mounted to the housing. In a sixth embodiment, the heater is chemical heating material adjacent the hole. In a seventh embodiment, the instrument has a distal portion adjacent the hole and a proximal portion remote from the hole and the heater is adjacent the proximal portion for heating the cells by heating treatment fluid remote from the distal portion. Other embodiments use infrared or ultrasound in order to heat patient cells.

Regardless of the heater arrangement, the instrument is preferably a catheter for insertion in a patient. The catheter further includes a flushing solution channel terminating in a flushing solution exit for applying flushing solution to a treatment site in a patient. The catheter includes a balloon mounted thereon and a balloon channel connected to the balloon for inflating the balloon, the balloon serving to occlude a body passage when the catheter is used for cell transfection.

The method of transfecting cells of a patient in vivo includes applying heat to the cells of the patient in vivo and providing a treatment agent including a DNA plasmid to the heated cells such that the heated cells are transfected. The application of heat is accomplished from one or more of the steps selected from the group including: application of laser energy to the cells, application of laser energy to heat an opaque portion of a part of an apparatus in thermal transfer position relative to the patient such that the apparatus in turn heats the cells, the application of radio frequency energy to the cells, application of microwave energy to the cells, electrically heating the cells, chemically heating the cells, heating the cells by infrared energy, heating the cells by ultrasound energy, and heating the treatment agent prior to its insertion in the patient such that the treatment agent heats the cells.

Preferably, the method further includes inserting a catheter into the patient, the catheter having a treatment agent channel, and wherein the heat is applied by way of the catheter and the treatment agent is provided by way of the treatment agent channel.

In one technique according to the present invention, heat is applied using application of laser energy exiting from the catheter in the form of a plurality of distinct beams including at least first and second beams which cause porations in the cells, the first beam applied to a first one of the cells when the second beam is applied to a second one of the cells.

Heat may be applied by use of laser energy exiting from the catheter in the form of a beam leaving the catheter with a width of less than 100 microns.

Heat may be applied by use of application of laser energy exiting from openings on a side of the catheter in the form of a plurality of beams, each leaving the catheter with a width of less than 100 microns, the plurality of beams causing porations in the cells, and the treatment agent is forced out the openings to follow multiple paths corresponding to the beams.

Heat may be applied by application of laser energy to heat an opaque portion of a part of the catheter in thermal transfer position relative to the patient such that the catheter in turn heats the cells.

BRIEF DESCRIPTION OF THE DRAWINGS

The above and other features of the present invention will be more readily understood when the following detailed description is considered in conjunction with the accompanying drawings wherein like characters represent like parts throughout the several views and in which.

DETAILED DESCRIPTION

Figure 1:
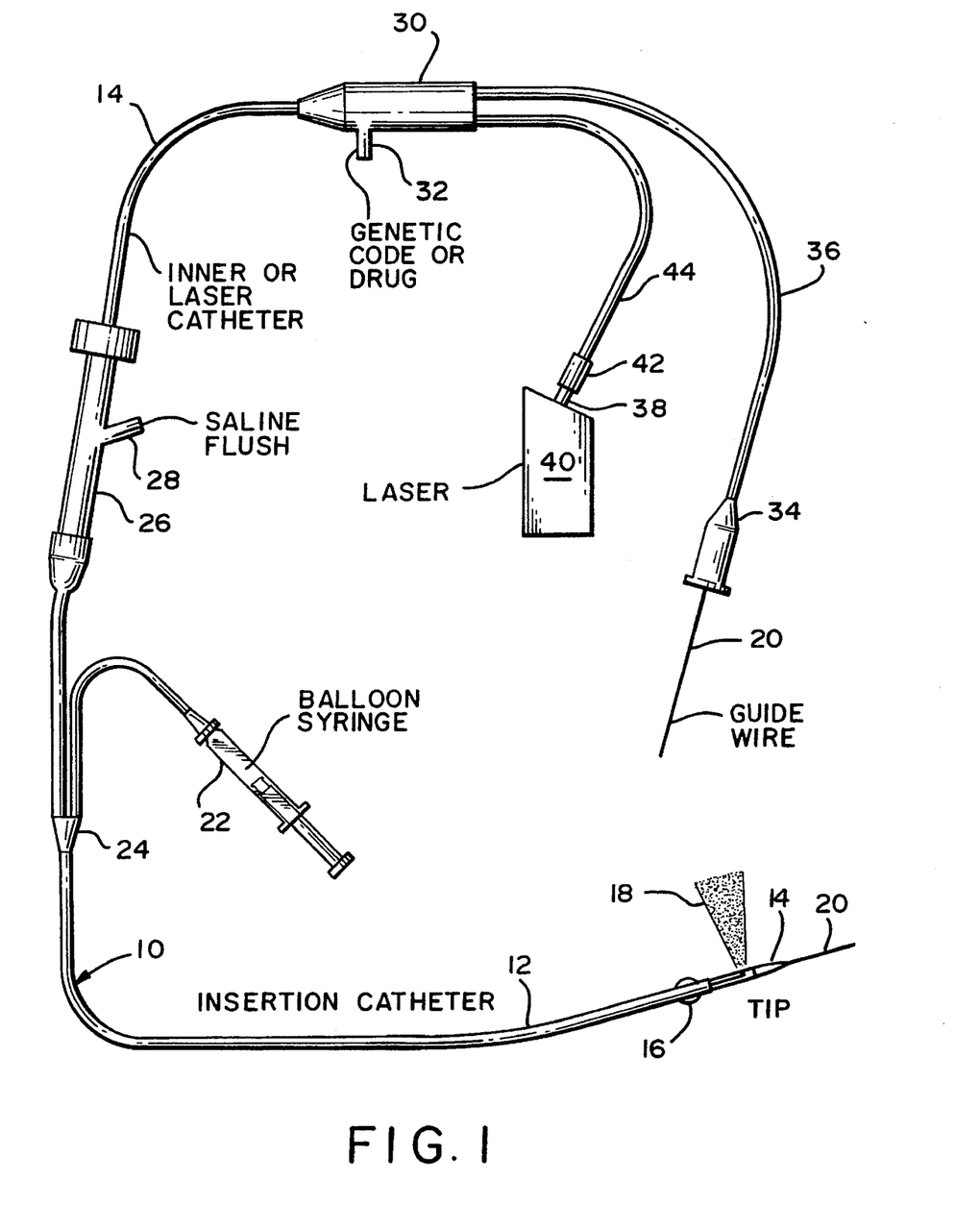
FIG. 1 shows a side view of a treatment catheter arrangement according to the present invention.

Turning initially to FIG. 1, a brief overview of the preferred embodiment of the present invention will be given. A treatment catheter 10, which might also be called a catheter assembly, includes an insertion catheter 12 and a laser catheter 14. The insertion catheter 12 has a balloon 16 mounted thereon for blocking blood flow in an artery, while the laser catheter 14 is applying laser energy 18 to porate cells (not shown) at the same time as genetic code material (not separately shown) is proceeding along the same paths as the laser energy 18. A guide wire 20 is used to guide the catheters to their intended location such that the laser energy 18 and associated genetic material may be applied to the proper site within the patient.

A balloon syringe 22 controls the balloon 16 in known fashion by way of a Y connection 24, which may be constructed in known fashion. Saline or other flush may be provided to the insertion catheter 12 by way of Y connector 26 having entry tube 28 for those purposes. The laser or inner catheter 14 is visible as it extends out the back of connector 26 towards the Y connector 30 having tube 32 for entry of genetic material or a drug to be inserted in the patient. A pump (not shown) or other arrangement may be connected to tube 32 to supply genetic material or a drug under pressure to inner catheter 14. The Y connector 30 is constructed in known fashion to merge the guide wire 20 (which proceeds from the luer lock or hemostatic Y-connector 34 and tube 36), optical fiber 38 (operably connected to laser 40 and proceeding through fiber connector 42 and tube 44), and the material inserted into the entry tube 32. Accordingly, the inner or laser catheter 14 proceeding out the left side of connector 30 includes the guide wire 20, the optical fiber (fiber optic element) 38, and any material supplied to the tube 32.

Figures 2, 2A, 3, 4, 5:
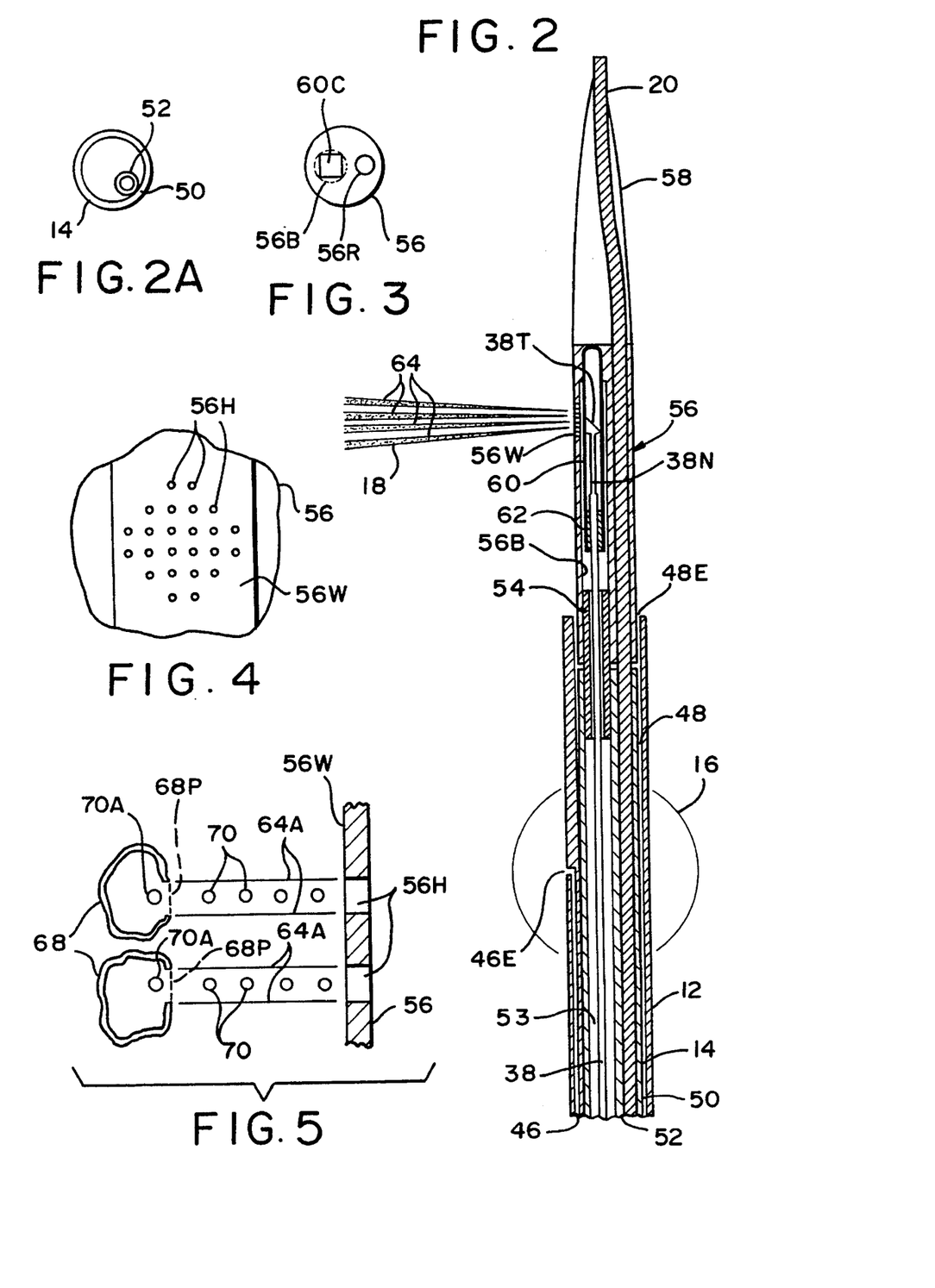
FIG. 2 shows a side view, with parts in cross section, of the treatment catheter or catheter assembly of FIG. 1.
FIG. 2A shows a simplified end view of the laser catheter.
FIG. 3 shows an end view of a tip of the arrangement of FIG. 2.
FIG. 4 shows a screen or window portion used to provide a plurality of very small beams of laser energy from a single larger beam of laser energy.
FIG. 5 shows a schematic view of a laser beam genetic code material being applied to different cells.

Turning now to FIG. 2, the details of the tip of the catheter arrangement of FIG. 1 will be explained. The insertion of flush catheter 12, which may be made of a common catheter material such as Teflon type material, is generally a hollow cylinder having a balloon control channel 46 separated from the main hollow part of the tubular catheter 12 and used to control the balloon 16 in known fashion by way of an exit 46E for the channel 46. A flushing solution channel 48, which is separate and distinct from the balloon channel 46, is disposed within the main hollow part of catheter 12. More specifically, the channel 48 may extend circumferentially in a ring just inside the wall of catheter 12 and outside of the inner or laser catheter 14. The channel 48 proceeds to a circumferential flush exit 48E.

The inner or laser catheter 14 has a generally cylindrical tube 50 of common flexible material used for catheters. Inside of the tube 50 is a guide wire tube 52 for slidably receiving the guide wire 20 therein. The tube 52, would be secured to one side of the tube 50 as best understood by momentarily turning to the end view of laser catheter 14 in FIG. 2A. Instead of having the tube 52 be distinct from tube 50, tube 52 might simply be a lengthwise extending pocket in tube 50 extruded at the same time as tube 50.

Turning back to FIG. 2, the optical fiber 38 extends inside of tube 50 and outside of tube 52 and extends into a connecting tube 54, which is preferably about 4 millimeters long and made of metal. The guide wire tube 52 and the connecting tube 54 would be glued, have barbs (not shown) to grip tube 50, or otherwise fixed in position (possibly simply by friction) within the tube 50. The connecting tube 54 secures a tip 56 to the tube 50. Specifically, the connecting tube 54 may be glued, friction-fit, snap fit using a ledge ring (not shown), or otherwise fixed to a cylindrical bore 56B within the tip 56. A second bore or cylindrical hole 56R (turn momentarily to FIG. 3) extends lengthwise in the tip 56. The tip 56, which is preferably made of surgical steel and is 8.7 millimeters long in the preferred embodiment, has a tapered end 58 which may be made of Teflon or other surgical materials commonly used in catheters. The tapered portion 58 would be hollow or otherwise allow for passage of guide wire 20 therethrough.

The optical fiber 38 proceeds through connecting tube 54 to a glass hood 60. Since the optical fiber 38 has a smaller outside diameter than the inner diameter of the hollow cylindrical connecting tube 54, an annular passage 54P is provided therebetween to allow fluid flow of treatment agent from an annular channel 53 into bore 56B. The optical fiber 38 is secured to the glass hood 60 by way of epoxy 62 applied after heating and creating a vacuum within the hood 60. The hood 60 preferably has a square cross section to fit within a square cross section cavity 60C (also refer momentarily to FIG. 3) which extends out from the circular bore or cavity 56B. Accordingly, the glass hood 60 may be adhered, friction-fit, or otherwise fixed within cavity 60C to prevent relative angular movement between the optical fiber 38 and the tip 56. The optical fiber 38 may have a portion of its cladding removed at its narrow portion 38N adjacent its end. The optical fiber 38 has a tip 38T to cause any laser beam to be directed sideways out a window portion 56W in the side of the wall of tip 56. More details of the construction of tip 38T and glass hood 60 may be obtained from U.S. Pat. No. 5,061,265, invented by the present inventor together with Stephan E. Friedl, issued on Oct. 29, 1991, and hereby incorporated by reference. Generally, the tip 38T is made into a prism using techniques described in that prior patent so as to deflect all, or substantially all, of the laser energy out the window portion 56W.

Continuing to view FIG. 2, but also referring to the enlarged view of the window portion 56W of tip 56 appearing in FIG. 4, the window portion 56W is essentially a laser screen having a plurality of very small holes 56H through which laser micro-beams 64 may pass. Thus, the window portion 56W may be considered as a grating portion having grating means, the grating means constituted by the holes or openings 56H and the material in between the holes 56H. The holes 56H would be distributed throughout an area of between one square millimeter and three square millimeters. Preferably, the holes are distributed evenly over a circular area of two square millimeters which would correspond to the width of the beam exiting from the tip 38T. Each of the holes 56H would be less than 200 microns. More specifically, the holes would be below 100 microns in diameter such that the micro-beams 64 would have a corresponding width as they leave the tip 56 of catheter 14. Most specifically, the holes would be 50 to 100 microns in diameter to provide beams of the same size. The holes 56H may be made by using an excimer laser or electrodischarge machine. The microbeams 64 would preferably have a diameter of 50 to 75 microns. As apparent from FIGS. 2 and 4, there are at least three beams which go in the same general direction. More specifically, at least 12 beams, corresponding to at least 12 holes, proceed out one side of the tip 56. As will be appreciated, there is a one-to-one correspondence between the beams 64 and the holes 56H. The beams 64 are distinct (i.e., meaning distinct where they leave the tip 56), but each of the beams 64 diverges somewhat because of the properties of the prism tip 38T of the optical fiber 38.

The openings 56H also allow passage of treatment agent which is supplied via treatment agent channel 53 (FIG. 2) in between fiber 38 and tube 50, connecting tube 54 (i.e., between tube 54 and fiber 38) and bore 56B.

Operation

Having described the structural features of the present invention, the method according to the present invention will now be described.

Although the present invention has applicability to providing treatment very efficiently on a cellular level at various sites on a patient's body or in a patient's body, the specifics of the structure which has been described is best suited for applying treatment to the walls of an artery and the explanation which follows will emphasize such an application of the invention.

A patient having an artery, such as a coronary artery, with atherosclerotic plaque is appropriately sedated and placed upon a x-ray or fluoroscopic table. Various know steps could be used for locating the tip 56 of laser catheter 14 at the site for treatment of the patient's artery and only a basic discussion of the procedure for locating the tip 56 at the proper site will be presented herein. Initially, the guide wire 20 and a guide catheter of common design (not shown) would be inserted into the patient using an introducer sheath of common design (not shown). The guide catheter would extend to the mouth of the artery, whereas the guide wire 20 would be manipulated to anchor its end just beyond the partial obstruction caused by the plaque.

The treatment catheter 10 (refer to FIG. 1), which includes both the laser or inner catheter 14 and the insertion or flush catheter 12 would then be slid along the guide wire 20. The catheters 12 and 14 would move along the guide catheter (not shown) in known fashion until the balloon 16 of the insertion catheter 12 is outside of the guide catheter and until the window portion 56W is adjacent the portion of the artery for which treatment is intended. The laser catheter 14 would be rotated until its window portion 56W (refer to FIG. 2) faces the side of the artery wall which is to be treated. The balloon 16 is then inflated using the balloon syringe 22 such that the part of the artery downstream (it would correspond to the rightward direction in FIG. 1) of balloon 16 is blocked from receiving further blood. The balloon 16 may be used to block the blood flow for up to about 60 seconds. The blockage would normally not need to be maintained for 60 seconds, but the surgeon would be using his professional judgement as to how long the blockage might be tolerated for a particular individual. At any rate, the blockage would be less than two minutes at a time and is significantly less than the blockage times required for the double balloon prior art technique described in the background portion of this application. If advisable, the balloon could be deflated and re-inflated to provide repeated treatments without maintaining the blockage for longer than about 60 seconds each time.

After the balloon 16 has been inflated and now considering FIGS. 1 and 2, a saline or other flushing solution is supplied to connector 26. The saline travels along the flushing solution channel 48 and exits from 48E (see especially FIG. 2) so as to clean out blood in the portion of the artery just downstream from the balloon 16. After this space has been flushed with saline, the saline flush is halted and the laser 40 is activated to generate the laser energy 18 (FIG. 1) in the form of the microbeams 64 (FIG. 2). The laser 40 would preferably be a pulsed laser pulsed at one to five times a second, such as a 355 nanometer tripled YAG or a flash lamp excited dye laser at 504 nanometers. However, a continuous wave argon laser or other type of laser might be used. A treatment agent will be supplied to the cells which are porated by the laser microbeams. A treatment agent as used herein is a cell treatment agent, meaning that it has medicinal effect (might include killing the cell if that was medically helpful) or harmful effect (if desirable for testing purposes) or remedial effect when placed within a cell after passing through porations caused by the laser microbeams. The treatment agent, such as genetic material or a drug is supplied to the connector 30 (FIG. 1) and passes through the treatment agent channel 53 and through the space between optical fiber 38 and connecting tube 54 into the hole or bore 56B for passage as a high pressure stream out of the window portion 56W. Referring now to FIG. 5, two cells 68 are shown having porations 68P therein as caused by the laser microbeams 64 having edges 64A shown in FIG. 5, the microbeams having passed out of holes 56H. Also passing out of the holes 56H is a high pressure solution containing the treatment agent 70 disposed therein and some of the treatment agent 70A has entered into the cells 68 by way of the porations 68P. If the agent 70 includes genetic materials, the solution may be culture material such as DMEM (Dulbecco's Modified Eagle's Medium) or normal saline. Quite importantly, the treatment agent 70 passes out of the same holes as the beams 64 such that the treatment agent passes along the same paths as the various microbeams 64. Accordingly, the genetic material should enter through the porations 68P in the cell walls of cells 68. In other words, the treatment agent is concentrated precisely where it is most likely to be effective. Significantly, the beam width is smaller than the size (i.e., longest dimension) of the cell and would also preferably be smaller than the normal dimension of the cell (i.e., the dimension of the cell extending perpendicular to the direction of the beam).

It should be appreciated that some of the microbeams 64 may hit the nucleus of a cell and kill the cell. Others of the microbeams may hit the edge of a cell without providing a useful poration. However, using a large number of the microbeams should allow for treatment, on a cellular level, of a sufficient number of cells that benefits will be obtained.

As an alternative to the simultaneous spraying of treatment agent 70 out of the holes 56H while the beams 64 are passing out of the holes, one might porate the cells 68 by application of the beams 64 and, immediately after turning off the beams 64, spray the treatment agent 70 out of the holes 56H. Since the porations 68P will close relatively quickly, the treatment agent should be sprayed immediately after turn off of the beams.

If one is simply treating a single part of the artery wall, one might line up the window portion 56W to face the proper direction by use of a marker (not shown) on part of the laser catheter 14. For example, a hole or pattern (not shown) might be placed on the side of steel tip 56 opposite to the window portion 56W. The surgeon would then observe the marker by use of the x-ray table and rotate the laser catheter 14 until the marker was opposite to the part of the artery wall which was to be treated. If desired, two markers of different configuration might be used to provide more information to the surgeon and to help better line up the window portion 56W such that it faces the part of the artery wall which is to be treated. Instead of placing the markers on the steel tip 56, the markers might alternately be placed upon the tapered portion 58 (which is made of plastic) and/or the outer surface of the laser catheter 14. If desired, one may treat the artery wall in a complete circumference. One may apply laser energy and treatment agent (either simultaneously or treatment agent immediately after laser as discussed above) with the laser catheter 14 disposed in one angular position. The laser would then be turned off, the laser catheter 14 would be rotated to a different angular position and the laser and treatment agent application would be repeated. The laser would be turned off and the laser catheter 14 would be rotated to another angular position for treatment. This process of rotation treatment followed by further rotation and treatment may be performed around the complete circumference of a portion of the artery. Additionally, or alternately, one may move the laser catheter 14 along the guide wire 20 to a different place within the artery before applying further treatment. In other words, if the blockage or other problem in the artery extends significantly in a lengthwise direction, treatments may be applied at different places along the length of the blockage.

Advantageously, a vacuum may be applied to tube 28 to remove genetic material or drug remaining free after laser operation and before deflating balloon 16. This reduces the amount of material going down stream.

After application of the laser beams and treatment agent has been completed, the balloon 16 would be deflated so as to reopen the artery. The treatment catheter 10 composed of laser catheter 14 and insertion catheter 12, is then removed from the patient. The guide catheter and guide wire would be removed from the patient and normal post-operative procedures would be followed such as checking the patient to insure that no artery walls were punctured.

Having shown how the present invention may be used to very efficiently provide treatment at a cellular level by injecting cell treatment agents 70 directly into cells 68 as illustrated in FIG. 5, some specific examples of such treatments using laser energy will now be presented. Generally, any genetic code material, such as DNA plasmids, and any drug applicable for cellular treatment could be used.

EXAMPLE 1

A patient has a buildup of plaque on the walls of a coronary artery. The treatment catheter 10 would be inserted into the patient under the procedure explained above and the microbeams 64 are used to porate smooth muscle cells of the artery walls. The treatment agent would be plasmids of DNA which encode antisense gene. The gene may be under the control of mouse metallothionein promotor. A virus carrier would be used in known fashion to allow the desired genetic material to enter the nucleus and/or cytoplasm (most frequently the cytoplasm) of the cells into which the treatment agent is inserted. The antisense genetic code will fool the smooth muscle cells to inhibit growth patterns which cause the blockage of arteries.

EXAMPLE 2

A patient has a buildup of plaque on the coronary arteries. The treatment catheter 10 would be inserted into the patient under the procedure described above and the microbeams 64 are used to porate the endothelial cells of the artery walls. The treatment agent would be plasmids of DNA which encode a tissue plasminogen activator gene under the control of the mouse promotor as with example 1 and having a virus carrier. The human plasminogen activator would cause the production of enzymes which reduce formation of clots.

EXAMPLE 3

A patient has a malignant tumor in the colon. The patient would be sedated and a colonoscopy would be performed. Instead of using an x-ray or fluoroscopic table to locate the position of the treatment device placed within the patient, the treatment device (not shown) may include an optical fiber to allow the surgeon to see within the colon. The probe or medical device inserted into the patient would include a laser catheter similar to catheter 14 of FIG. 2. Upon the window portion (similar to 56W of FIG. 2) being lined up to face the tumor, laser energy is applied to provide microbeams which porate the cells of the tumor and a cancer agent, such as 5-fluorouracil or donarubicin, is injected out the same plurality of holes used for generating the microbeams. Saline or other solution may be used to carry the cancer agent drug to the cells. The cancer agent would enter into numerous of the cancer cells and kill them. Advantageously, the poration of the cells by the laser beam improves the efficiency of application of the cancer agent to the cells. A smaller portion of the cancer agent harms adjacent healthy cells than would be the case if one simply applied the cancer agent against cells which had not been porated. Some of the cancer cells may be killed simply by application of the laser beam, but the inclusion of the cancer agent helps to kill a greater portion of the cancer cells than would otherwise be the case. Additionally, if one simply relied upon the laser to kill cancer cells, one might have to use a higher laser power which in turn might damage healthy cells behind or adjacent to the cancer cells.

EXAMPLE 4

The patient would be the same as in example 2 and the same procedure would be followed except that the treatment agent is the drug heparin carried by saline or other solution. The drug prevents formation of clots.

EXAMPLE 5

An animal may be used to test various anti-plaque techniques by using the present invention to induce plaque in walls of arteries. The treatment catheter 10 is used to porate endothelial cells on artery walls of the animal (patient) for introducing a plasmid of DNA which encodes for human growth hormone gene under the control of a mouse metallothionein promoter. A viral carrier would be used in known fashion to allow the desired genetic material to enter the nucleus and/or cytoplasm of the cells into which the treatment agent is inserted. The expression of growth hormone in transfected cells will then result in the expression of various cellular proteins causing cell growth which could be responsible in part for the development of plaque in the arterial wall. This information could then be used to develop either drugs or other methods to inhibit gene expression in order to block this growth.

Figure 6:
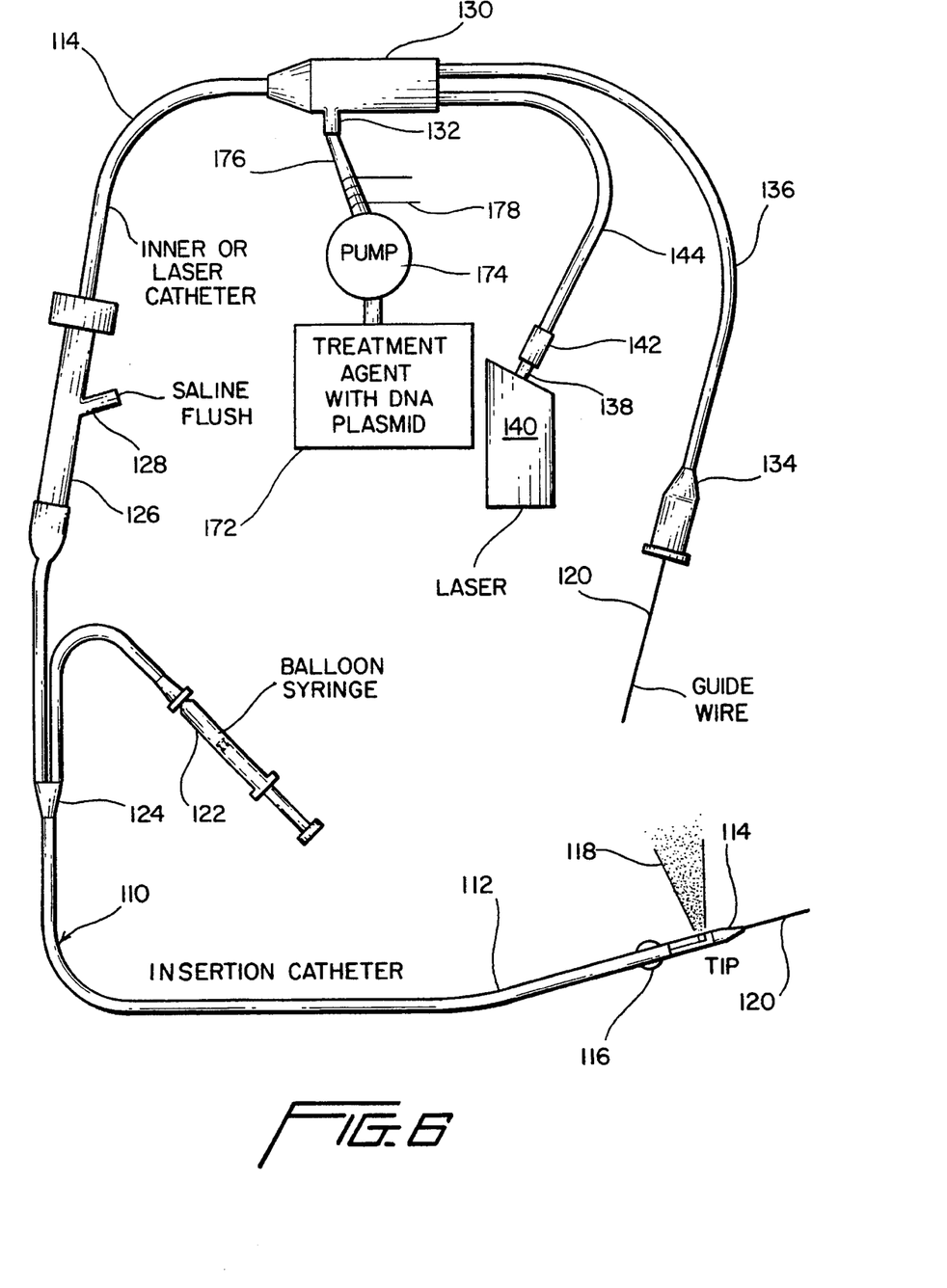
FIG. 6 shows a side view of a second embodiment catheter according to the present invention.

Turning now to FIG. 6, an alternate embodiment constructed in somewhat similar fashion to the embodiment of FIG. 1 will be discussed. The components of the FIG. 6 embodiment have numbers in the 100 series with the same last two digits as the corresponding component, if any, of the FIG. 1 embodiment. Thus, the components 110 through 144 are identical in construction and operation as the corresponding components in FIG. 1 except as discussed hereafter.

As shown, a reservoir 172 of treatment agent with DNA plasmid is connected to pump 174. The pump 174 pumps the agent into entry tube 132 by way of tube 176. This operation as described so far is identical to the catheter 10 of FIG. 1 where the reservoir and pump were simply not shown. What is different about the catheter system 110 is the use of an electrical heating coil 178 wrapped around the tube 176 in order to heat the agent prior to its insertion in the patient. By heating the agent sufficiently that the agent adjacent the patient's cells will be from 42 degrees to 45 degrees, the transfection process is speeded up and will occur faster than would otherwise be the case. Indeed, the laser 140 and laser catheter 114 could be left out of the apparatus 110 and the heat from electrical heater 178 could be used without laser energy in order to expedite the transfection process. In that case, a catheter 114 could be constructed like catheter 14 of FIG. 2 except that there would be no optical fiber such as 38 of FIG. 2. Also, such an arrangement could use one of more large exit holes instead of the array of 50 to 100 micron diameter holes 56H of FIG. 4.

Although the heater 178 is shown as a coil heater, other electrical or non-electric heating techniques could be used to heat the agent either prior to its insertion in the catheter 110 or while it is traveling therein.

Figure 7:
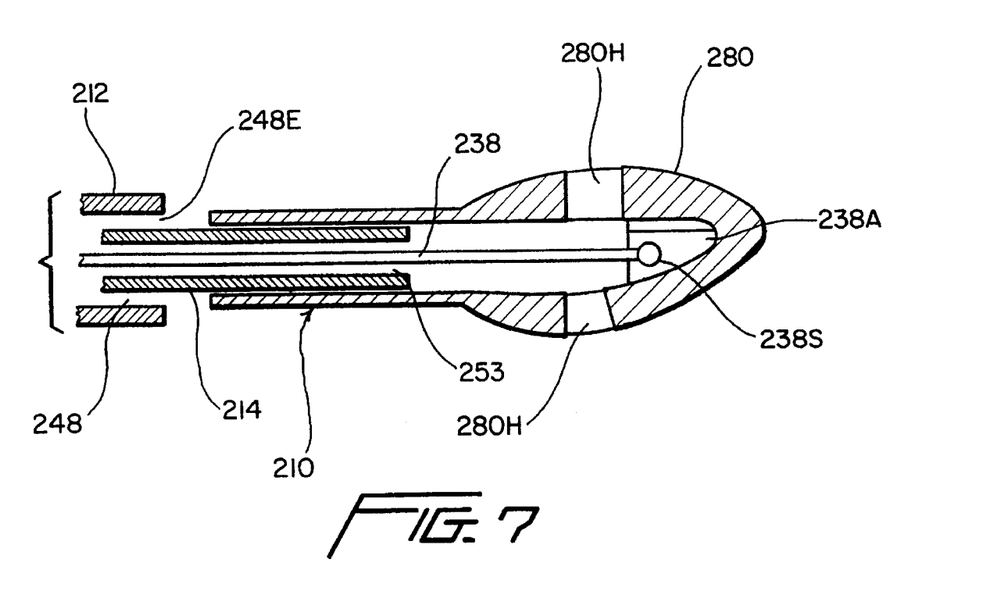
FIG. 7 shows a simplified side view with parts in cross-section of a distal end of a third embodiment catheter.

FIG. 7 shows an embodiment using application of laser energy to heat the tip of catheter 210 and thereby indirectly heat the cells. The components of the FIG. 7 embodiment have numbers in the 200 series with the same last two digits as the corresponding component, if any, of the FIG. 1 embodiment. Insertion catheter 212, laser catheter 214, optical fiber 238, flushing solution channel 248, flushing solution exit 248E, and treatment agent channel 253 function as the corresponding components in the previous embodiments except as discussed below. (The unseen parts of catheter 210 would be connected to a laser and a source of treatment agent with DNA plasmid as with previous embodiments.)

The FIG. 7 embodiment is different from the others in that it has an opaque metal cap 280 with neck portion 280N crimped or otherwise fixed to catheter 214. The metal may be similar to metal parts 50 in FIG. 4 and 70 in FIG. 5 of the present inventor's U.S. Pat. No. 5,041,109, patent, issued Aug. 20, 1991, and hereby incorporated by reference in its entirety. Cap 280 has holes 280H for treatment agent to exit from, whereas optic fiber 238 terminates in a spherical lens 238S which distributes laser energy, not shown, over a wide area of cap 280. Arms 238A may be circumferentially arranged to support fiber 238. The laser energy heats the cap 280, which in turn would heat the patient's cells (not shown) and make them more receptive to transfection from the treatment agent.

Although not shown in the FIG. 7 embodiment, one or more occluder balloons such as 16 of FIG. 1 could be used in the FIG. 7 embodiment and the embodiments hereafter discussed. For ease of illustration, the insertion catheter, such as 212 of FIG. 7, and flushing solution channel will not be shown or discussed for the embodiments discussed below, even though those embodiments would have such features.

Figure 8:
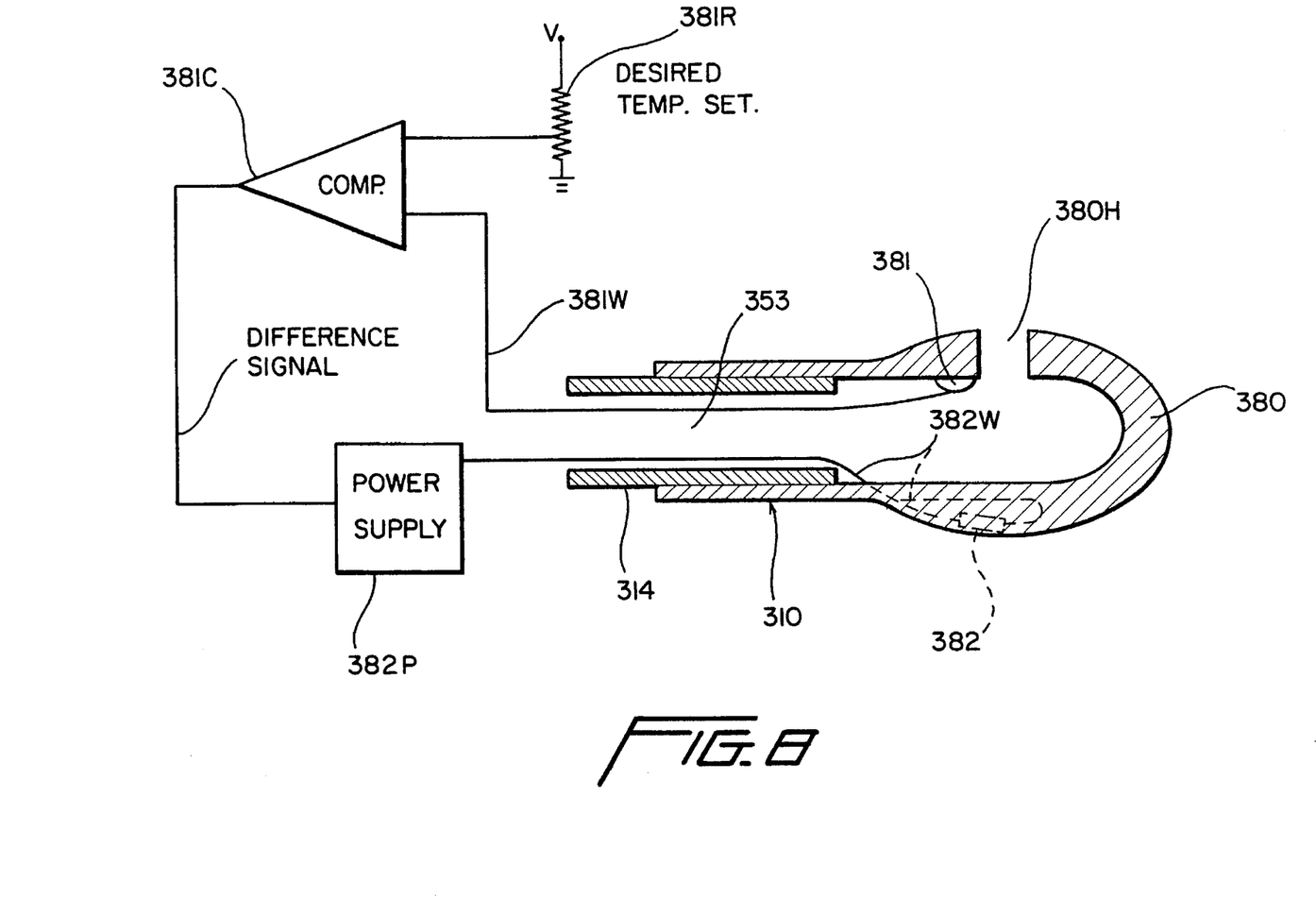
FIG. 8 shows a simplified side view with parts in cross-section of a distal end of a fourth embodiment catheter.

Catheter 310 of FIG. 8 has numbers in the 300 series with the same last two digits as the corresponding component, if any, of the earlier embodiments. This embodiment has a cap 380 with hole 380H for dispersing treatment agent from channel 353. A thermocouple or other temperature sensing device 381 has wires 381W (only one shown for ease of illustration) extending out of catheter 310; The cap 380 has at least one heating resistor 382 embedded therein or otherwise in thermal contact therewith. The resistor 382 serves as a heat source. Wires 382W (only one shown for ease of illustration) carry electrical current from a power supply 382P external outside of the patient to the heater resistor 382. The power supply 382P is part of a feedback control closed loop which uses negative feedback by way of temperature adjustor resistor 381R and comparator 381C. As well known such a control loop could alternately use an amplifier, subtractor, or adder (instead of comparator 381C) to generate a difference signal at the output thereof to cause the heater resistor 382 to heat more if the temperature is low and to heat less if the temperature is too high. Since thermocouple or other sensor 381 is located near the hole 380, it will very accurately track the temperature of treatment agent fluid passing out the hole 380H. Preferably, the sensor 381 is within at least 5 inches of hole 380H, and more preferably and advantageously within 3 inches thereof. Most preferably, it is at the edge of hole 380H or within 1 inch of the edge of the hole.

The feedback circuit may be configured differently from FIG. 8 as many types of thermostatic or other feedback techniques are known for stabilizing a sensed condition such as temperature. It should be emphasized that the feedback control to maintain the fluid temperature shown for FIG. 8 would preferably be used for the various other embodiments discussed above and below. Such feedback control loops and components are not shown for the other embodiments for ease of illustration. However, all embodiments may use a temperature dependent sensor on the catheter as discussed to control the output of the heating device or devices so as to maintain the temperature at a desired value or within a desired range, which is preferably 42 to 45 degrees centigrade.

The heater resistor 382 may be of the CAL-ROD type or any other device generating heat from electricity. The cap 380 may be metal like cap 280 or could be other material suitable to disperse heat to patient's cells adjacent to the window 380H. As with the other embodiments not based on direct application of laser energy to the patient's cells, the heat could be used to heat the patient's cells to from 42 to 45 degrees centigrade and enhance their receptivity to transfection.

Figure 9:
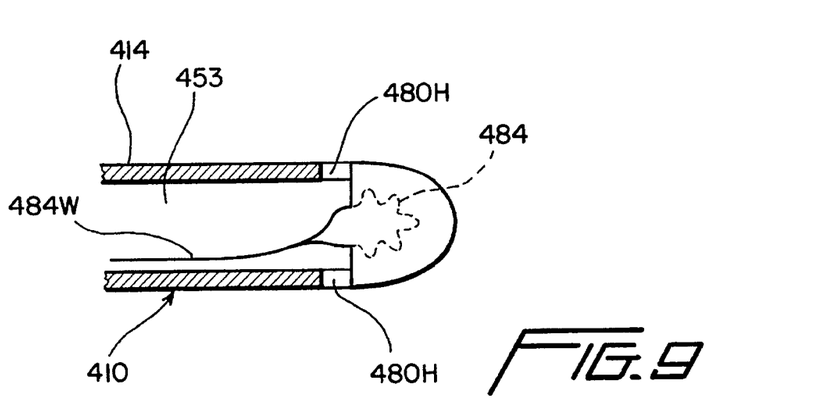
FIG. 9 shows a simplified side view with parts in cross-section of a distal end of a fifth embodiment catheter.

Catheter 410 of FIG. 9 has numbers in the 400 series with the same last two digits as the corresponding component, if any, of the earlier embodiments. Inner catheter 414 has holes 480H to allow exit of treatment agent from treatment agent channel 353. Radio frequency (RF) waves are emitted from antenna 484 or other known RF source. Wires 484W are connected to supply power as appropriate to antenna 484, which is embedded in part 414E. Part 414E may simply be a generally cylindrical rounded tip of the material making up the side of catheter 414 (and sides of the various other catheter embodiments), which material may be PTFE (such as Teflon) or other materials commonly used for catheters. The RF energy is used in this embodiment to heat the patient's cells, preferably to 42 to 45 degrees centigrade, in order to make them more receptive to transfection.

Figure 10:
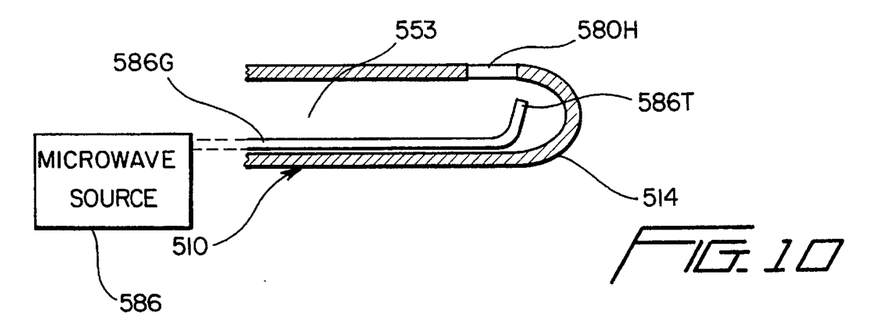
FIG. 10 shows a simplified side view with parts in cross-section of a distal end of a sixth embodiment catheter.

The FIG. 10 embodiment of catheter 510 uses microwave energy from source 586 outside the patient to heat cells for improving receptivity to transfection. Microwave source 586 supplies microwave energy to inner catheter 514 by way of waveguide 586G for exiting at a microwave output tip 586T. The microwave energy is applied to patient's cells (not shown) adjacent hole 580H from which treatment agent from channel 553 may exit.

Figure 11:
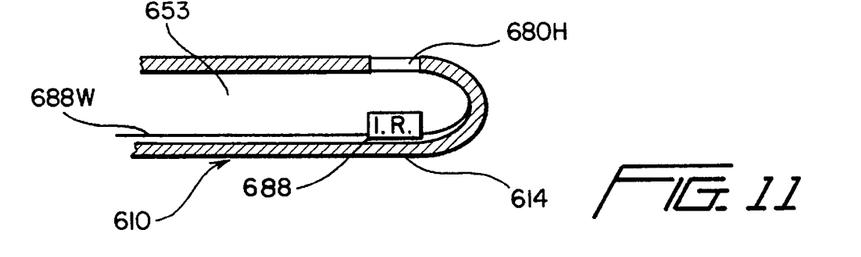
FIG. 11 shows a simplified side view with parts in cross-section of a distal end of a seventh embodiment catheter.

FIG. 11 shows catheter 610 with inner catheter 614 having an infrared source 688 connected by wires 688W to a power source (not shown) outside the patient. Infrared energy from source 688 heats treatment fluid and/or the patient's cells (not shown) as treatment agent from channel 653 exits hole 680H.

Figure 12:
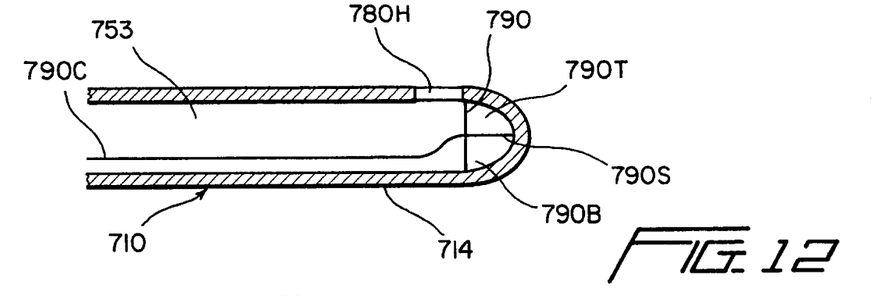
FIG. 12 shows a simplified side view with parts in cross-section of a distal end of a eighth embodiment catheter.

The catheter 710 of FIG. 12 has an inner catheter 714 with a treatment agent channel 753 supplying treatment agent out hole 780H. In this embodiment a chemical compartment behind (right in FIG. 12) wall 790 is divided into top and bottom parts 790T and 790B by separation wall 790S. Parts 790T and 790B hold different chemicals which react to release heat when they mix upon control line 790C being used to slide separation wall 790S leftwardly in FIG. 12. The heat heats patient cells to improve receptivity to transfection.

Figure 13:
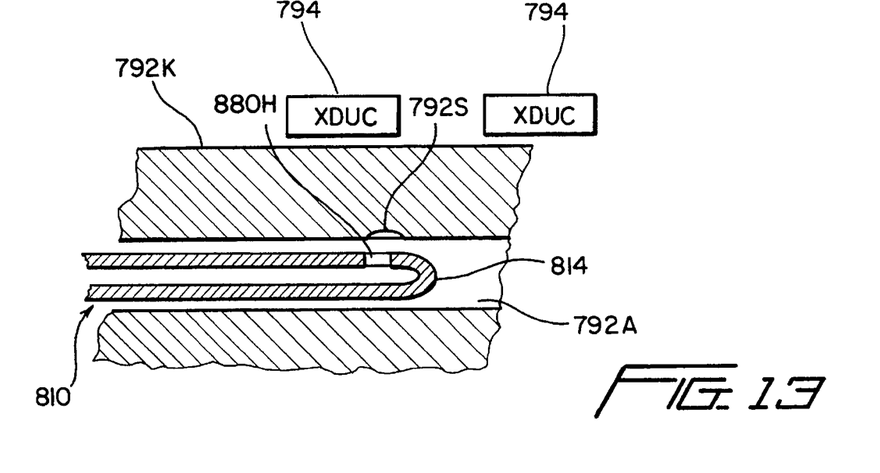
FIG. 13 shows a simplified side view with parts in cross-section of a distal end of a ninth embodiment catheter with parts of a patient.

FIG. 13 shows a catheter 810 with inner catheter 814 having hole 880H for releasing treatment agent to a site 792S within a patient's artery (or other body passage) 792A. In this arrangement the cells at site 792S are heated by application of ultrasound energy from transducers 794 on the skin 792K of the patient.

Turning now to FIGS. 14–17, a further embodiment catheter 910 has a tip 956 with tapered portion 958. A guide wire 920 is used and a glass hood 960 is used. The components of catheter 910 and other unshown components may be constructed and may operate as the corresponding component (same last two digits) from FIGS. 1–6. This discussion will proceed with differences between catheter 910 and catheter 10.

Catheter 910 has a window 956W which is simply one large opening. Instead of relying on holes to produce microbeams of laser energy for cell poration as done in the embodiment of FIGS. 1–6, catheter 910 uses a bundle 995 having a sloped tip 995S and a plurality of optical fibers 938 (only some numbered for use of illustration) with filler material 995C. At least the portions adjacent to slope 995S of the filler material should be clear such that beams 964 may emerge from the tips 938T (shown schematically in FIG. 14 only). Each tip 938T may provide a single corresponding beam 964, which beam may have dimensions and operate as discussed for each of the beams 64 of FIG. 2. As illustrated schematically in the front view of FIG. 14, the tips 938T and fibers 938 are staggered such that light from one tip 938T will not hit another of the tips 938T or fibers 938 on its way to the single opening window 956W and the patient tissue outside it.

Figures 14, 15, 16, 17:
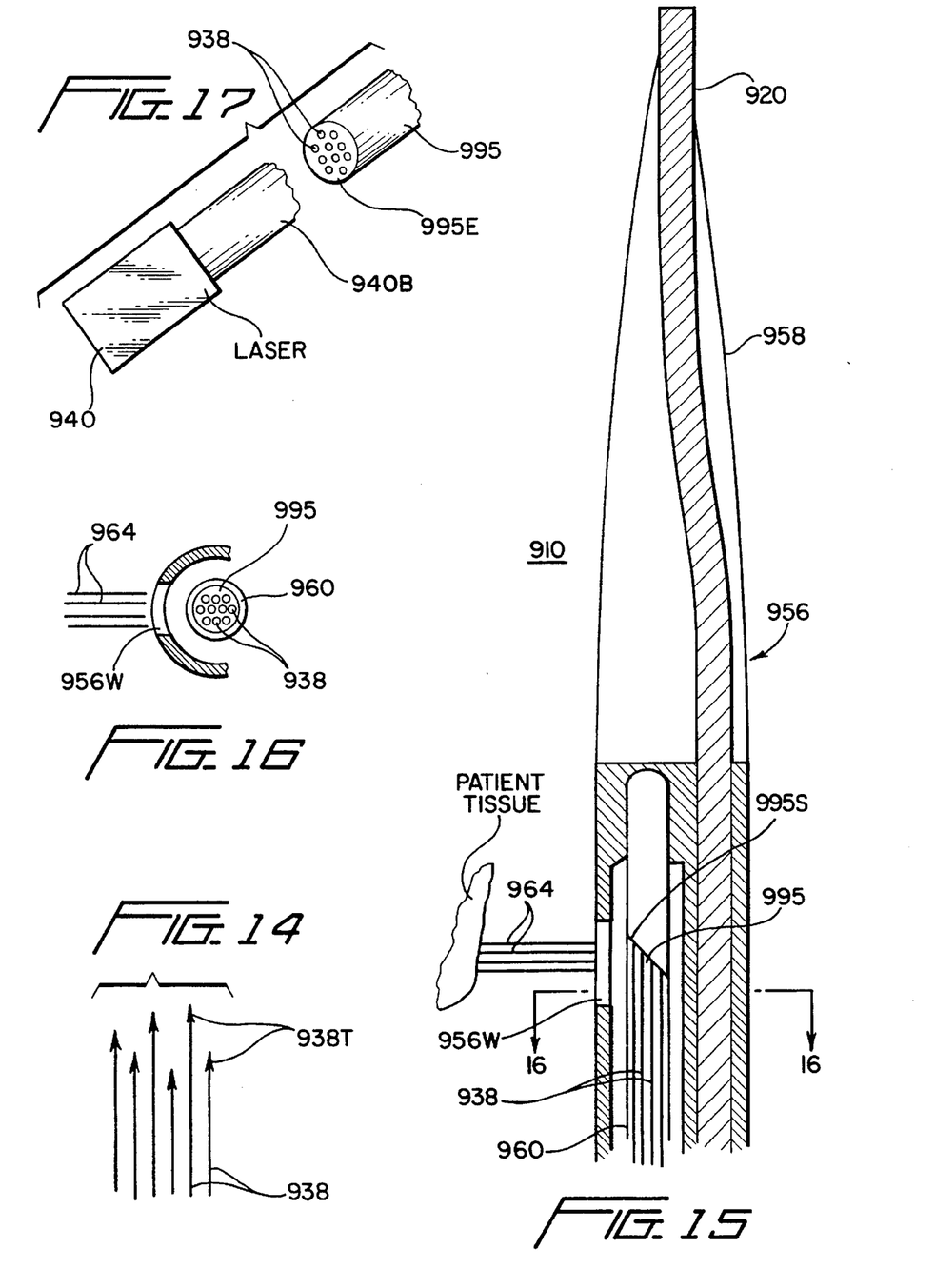
FIG. 14 shows a simplified front view schematic to illustrate staggering of various fibers in yet another embodiment.
FIG. 15 is a side view with parts in cross section of a catheter using the staggering feature of FIG. 14.
FIG. 16 is a cross section with parts removed for simplicity taken along line 16—16 of FIG. 15.
FIG. 17 shows a perspective of an external end of a fiber optic bundle corresponding to the FIG. 15 combined with a schematic illustrating how laser energy is applied to the bundle.

The laser energy at the tips 938T is reflected out the window 956W by either of two arrangements. A first way is to simply have the optical fiber tips 938T cut at the same angle (preferably between 35 and 55 degrees, most preferably an angle from 42 to 48 degrees, with 45 degrees being the most preferred value) as the slope 995S. (The angle being measured relative to a horizontal line, not shown, perpendicular to the axes of the parallel optical fibers 938.) This first way has tips which reflect light such that it goes in the direction from a low end of the sloped face towards the high end of the sloped fiber tip. A second way is to have a prism such as shown and explained for the tip of FIG. 7 of the incorporated by reference U.S. Pat. No. 5,061,265.

FIG. 17 shows the external end 995E of bundle 995 receiving a laser beam 940B from a laser 940. Since the optical fibers are relatively small, they will produce a plurality of beams having the width ranges as discussed with respect to the embodiment of FIGS. 1–6. The optical fibers themselves may have diameters equal to the various ranges discussed with respect to the beam widths given above dimensions with respect to the embodiment of FIGS. 1–6. The optical fibers may be 80 microns in diameter. As in the other drawings, only a relatively small number of fibers 938 are shown, but it will be understood that the number of fibers could be just a few or a relatively large number.

A further alternate to the arrangement of FIGS. 14–17 may be discussed with reference to FIG. 16 since such a further embodiment might be constructed as with FIGS. 14–17 and have essentially the same top view. The beam pattern of FIG. 16 might be realized by plurality of fibers with prisms at their tips and with all the tips ending in the same plane perpendicular to the axes of the fibers and the catheter. Further, such prisms could alternately direct the beams radially outward from a 5 central axis of a bundle such as 995S.

Figure 18:
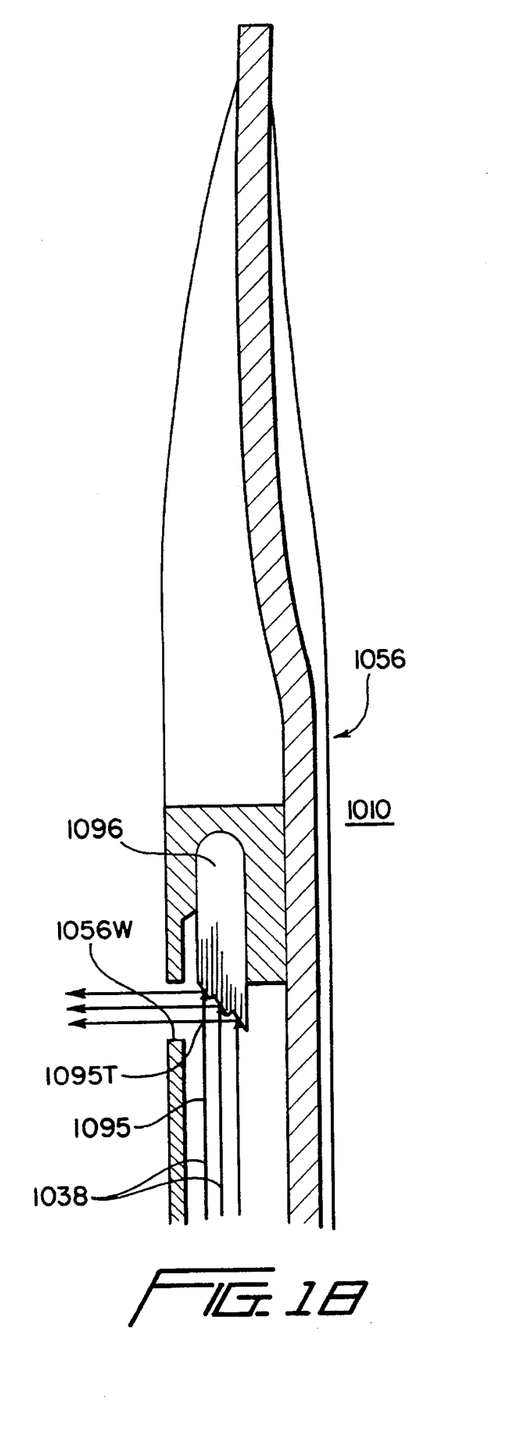
FIG. 18 is a side view with parts in cross section of a catheter using a reflector.
Figure 19:
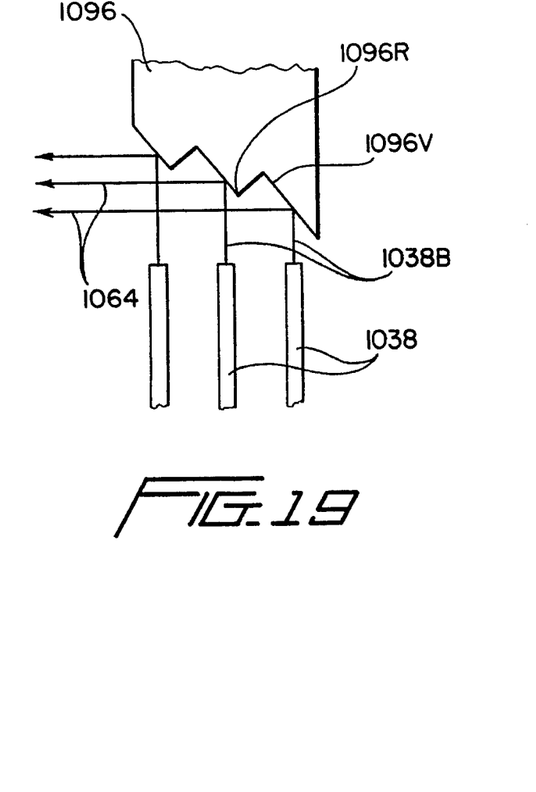
FIG. 19 is a detailed side view of the reflector and optical fibers of FIG. 18.

Turning now to FIGS. 18 and 19, catheter 1010 has a tip 1056 and bundle 1095 operating and constructed as with the FIG. 15 embodiment except as follows. The bundle 1095 has a flat tip end 1095T from which beams 1038B pass from a plurality of fibers 1038 to a reflector 1096, which may be either a piece of silicon glass or a mirrored reflector. The reflector 1096 may be made and operate in the fashion explained in Saadatmanesh et al. U.S. Pat. No. 5,242,438, issued Sep. 7, 1993 and hereby incorporated by reference except that the present reflector is shaped differently as discussed hereafter.

The reflector 1096 has a series of parallel ridges 1096R and valleys 1096V extending across reflector 1096 perpendicular to the plane of view of FIGS. 18 and 19. The ridges and valleys are stepped in that those closest the one-hole window 1056W are further from tip end 1095T than the ridges and valleys which are further from the window 1056W. Since the slopes between ridges 1096R and valleys 1096V which face the window 1056W have a 45 degree slope relative to beams 1038 (corresponding to the axes of fibers 1038), beams 1038 are reflected at right angles (90 degrees) becoming beams 1064. The beam widths for beams 1064 would be as discussed with respect to FIGS. 1–6.

Figure 20:
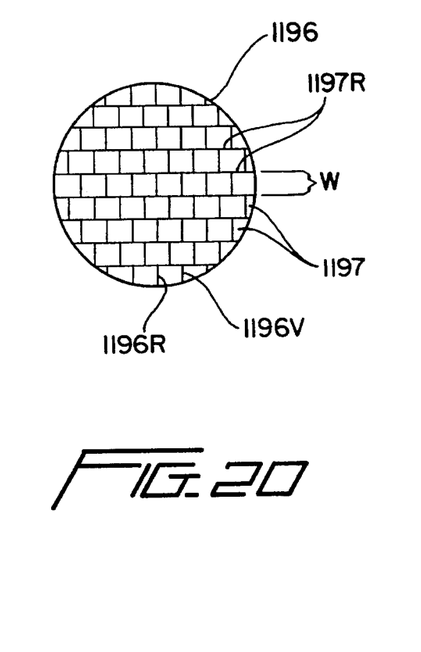
FIG. 20 is a view of the face of an alternate reflector used to split a relatively broad beam into a plurality of small width beams.

FIG. 20 shows a bottom view (i.e., side receiving laser energy) of an alternate reflector 1196 similar in operation and construction as reflector 1096 except as follows. Reflector 1196 has a plurality of rows 1197 of width W, each row having stepped ridges 1196R and valleys 1196V such that a cross section along or parallel to any of lines 1197R (which separate adjacent rows) reveals a profile like that presented by reflector 1096 in FIG. 19. By using a plurality of the rows 1197, a single optical fiber like fiber 38 of FIG. 2 (but without a prism at its tip) could apply a relatively wide beam to reflector 1196. The reflector 1196 would receive such a single beam (not shown) exiting in line with the central axis of the single optical fiber and create multiple beams by reflection. The reflection would be accomplished as discussed for FIG. 19 except that the reflection would actually be separating a relatively wide beam into a plurality of beams (not shown). The beam widths would be as discussed with respect to FIGS. 1–6.

It will be readily appreciated that the embodiments of FIGS. 7 to 20 would be constructed in the same fashion as the FIGS. 1 to 6 embodiments except for the illustrated differences. All of the embodiments which heat the patient's cells in vivo without direct application of laser energy to the cells would heat the cells to 42 to 45 degrees centigrade for improving transfection receptivity. All of the embodiments may use one or two occluder balloons as discussed in connection with the FIG. 1 embodiment and may use feedback control as discussed with respect to FIG. 8. Although the discussion of FIGS. 6 to 20 has concentrated on DNA plasmids for treatment, drugs or other materials could be used. The treatment agent may have plasmids coprecipitated with $CaPO_4$ or some other catalyst as that may be at least advisable to improve transfection.

Tests by the present inventor of in vitro transfection into bovine aorta smooth muscle cells (SMC) have shown that heat can increase the efficiency of transfection. The plasmid pXGH5, which encodes a human growth hormone (hGH) reporter, was used to determine efficiency of transfection. SMC transfection was performed using DNA coprecipitated with $CaPO_4$. SMCs were immediately heated for up to 1 hour at 42 to 45 degrees centigrade. Results were compared to paired control experiments conducted on the same day in the absence of heating. Transient gene expression was determined by radioimmunoassay of spent medium for hGH 48 hours after transfection. SMCs heated and exposed to DNA without $CaPO_4$ showed no gene expression. In the 60 paired experiments, SMCs transfected by $CaPO_4$ coprecipitation of DNA and heated demonstrated an increased hGH production compared to unheated controls, 20.3 plus or minus 3.7 versus 16.8 plus or minus 3.4 (mean plus or minus SE) respectively, $p<0.002$.

With respect to the various embodiments applying laser energy to the tissues of a patient, one may use an external chromophore which will absorb wavelengths selectively to raise the temperature of the desired tissue. This would selectively heat the target tissue and reduce heat applied to other tissues. Also, it should smooth out the process of heating (i.e., avoid too fast temperature changes) and provide a more even temperature distribution over the desired tissues. Such a chromophore may involve oral or intravenous injection of materials which will concentrate in the desired tissues and make them more receptive to laser heating. Also, such materials to increase receptivity to laser heating may be inserted in the channel or channels of the catheter to be directly applied adjacent the heating.

Although specific constructions and examples have been presented herein, it is to be understood that these are for illustrative purposes only. Various modifications and adaptations will be apparent to those of skill in the art. For example, one might use a double balloon catheter with the laser beams and treatment agents being applied from a window portion in between two balloons. Although the present invention has the highly advantageous feature of injecting the treatment agents out the same holes as the laser beams, the present invention, in its broadest aspects, might include a double balloon arrangement wherein the treatment agent comes out holes separate from the laser beams and fills the chamber established between the two balloons blocking part of an artery. Since the laser beams would be porating the cells within artery walls between two such balloons, the treatment agent, such as genetic material, could transfect the cells more quickly than in the prior art double balloon technique discussed in the background portion of this application since that prior art technique did not provide for cell porations. Such a double balloon technique may also use known dye materials inserted to enhance absorption of laser energy. Such materials are disclosed in the present inventors' prior U.S. Pat. Nos. 4,860,743 and 5,041,109 issued respectively on Aug. 29, 1989 and Aug. 20, 1991 and hereby incorporated by reference. Although the laser 40 would preferably be a pulsed type laser which could use feedback control as discussed, one would especially want to use a thermocouple (for feedback control as discussed) to guard against overheating if the laser 40 was a continuous wave laser. In view of these and other possible modifications, it will be appreciated that the scope of the present invention should be determined by reference to the claims appended hereto.

What is claimed is:

1. An apparatus for cell transfection comprising:
   an instrument with a housing having a wall with at least one hole therein, wherein said instrument has a distal portion adjacent said hole and a proximal portion remote from said hole;
   a heater operatively connected to said distal portion so as to apply a sufficient amount of heat to cells of a patient in vivo to enhance the cells susceptibility to transfection; and
   a source of treatment agent including a DNA plasmid operatively connected to the instrument so as to apply treatment agent to the heated cells by way of a treatment channel inside said instrument and extending to said hole; and
   wherein the treatment agent is operable to transfect the heated cells.

2. The apparatus of claim 1 wherein said heater includes an optical fiber within said instrument for applying laser energy by way of said hole to heat the cells.

3. The apparatus of claim 1 wherein said heater includes an optical fiber within said instrument for heating an opaque portion of the instrument such that the opaque portion in turn heats the cells.

4. The apparatus of claim 1 wherein said heater is an RF source at the distal portion and which heats the cells by application of radio frequency energy.

5. The apparatus of claim 1 wherein said heater is a microwave source with a microwave output at the distal portion and which heats the cells by application of microwave energy.

6. The apparatus of claim 1 wherein said heater is an electrical heater mounted to said housing, said electrical heater having a heat source at said distal portion.

7. The apparatus of claim 1 wherein said heater is chemical heating material adjacent said hole.

8. The apparatus of claim 1 wherein said heater is adjacent said proximal portion for heating the cells by heating treatment fluid remote from said distal portion, and further comprising means to supply treatment fluid to said hole, which treatment fluid in turn carries heat to the cells of the patient in vivo.

9. The apparatus of claim 1 wherein said instrument is a catheter for insertion in a patient.

10. The apparatus of claim 9 wherein said catheter further includes a flushing solution channel terminating in a flushing solution exit for applying flushing solution to a treatment site in a patient.

11. The apparatus of claim 10 wherein said catheter includes a balloon mounted thereon and a balloon channel connected to said balloon for inflating said balloon, said balloon serving to occlude a body passage when the catheter is used for cell transfection.

12. The apparatus of claim 1 further comprising a reflector and wherein said heater includes at least one optical fiber within said instrument for applying laser energy by way of said reflector and said hole to heat the cells.

13. The apparatus of claim 12 wherein said heater includes a plurality of optical fibers within said instrument for applying laser energy by way of said reflector and said hole to heat the cells by a plurality of beams, each beam corresponding to one of said optical fibers.

14. An apparatus for cell transfection comprising:
   a catheter with a housing having a wall with at least one hole therein, wherein said catheter has a distal portion adjacent said hole and a proximal portion remote from said hole;
   a heating means operatively connected to the distal portion of said catheter so as to apply a sufficient amount of heat to cells of a patient in vivo to enhance the cells susceptibility to transfection; and
   a source of treatment agent including a DNA plasmid operatively connected to said catheter so as to apply treatment agent to the heated cells by way of a treatment channel inside said catheter and extending to said hole; and
   wherein the treatment agent is operable to transfect the heated cells.

15. The apparatus of claim 14 wherein said heating means includes an optical fiber within said catheter for applying laser energy by way of said hole to heat the cells.

16. The apparatus of claim 14 wherein said heating means includes an optical fiber within said catheter for heating an opaque portion of the catheter such that the opaque portion in turn heats the cells.

17. The apparatus of claim 14 wherein said heating means is an RF source at the distal portion and which heats the cells by application of radio frequency energy.

18. The apparatus of claim 14 wherein said heating means is a microwave source with a microwave output at the distal portion and which heats the cells by application of microwave energy.

19. The apparatus of claim 14 wherein said heating means is an electrical heating means mounted to said housing, said electrical heater having a heat source at said distal portion.

20. The apparatus of claim 14 wherein said heating means is chemical heating material adjacent said hole.

21. The apparatus of claim 14 wherein said heating means is adjacent said proximal portion for heating the cells by heating treatment fluid remote from said distal portion, and further comprising means to supply treatment fluid to said hole, which treatment fluid in turn carries heat to the cells of the patient in vivo.

22. The apparatus of claim 14 wherein the heating means is disposed and operable to heat fluid, which fluid passes out said hole, and wherein the heating means heats the cells of the patient by way of fluid which has passed out said hole and further comprising: a temperature sensor on said catheter positioned to sense fluid temperature adjacent said hole; and a feedback control loop connecting said temperature sensor to said heating means and operable to stabilize the temperature of fluid passing out said hole.

23. A method of treating cells of a patient in vivo comprising the steps of:
   providing a device operable to apply heat and treatment agent to cells of a patient;
   applying heat to the cells of the patient in vivo by use of the device; and
   using the device to provide a treatment agent including a DNA plasmid to the heated cells such that the heated cells are transfected.

24. The method of claim 23 wherein the step of applying heat is accomplished from one or more of the steps selected from the group consisting of: application of laser energy to the cells, application of laser energy to heat an opaque portion of a part of an apparatus in thermal transfer position relative to the patient such that the apparatus in turn heats the cells, the application of radio frequency energy to the cells, application of microwave energy to the cells, electrically heating the cells, chemically heating the cells, heating the cells by infrared energy, heating the cells by ultrasound energy, and heating the treatment agent prior to its insertion in the patient such that the treatment agent heats the cells.

25. The method of claim 23 further comprising the step of inserting a catheter into the patient, the catheter having a treatment agent channel, and wherein the heat is applied by way of the catheter and the treatment agent is provided by way of the treatment agent channel.

26. The method of claim 25 wherein the step of applying heat uses application of laser energy exiting from the catheter in the form of a plurality of distinct beams including at least first and second beams which cause porations in the cells, said first beam applied to a first one of said cells when said second beam is applied to a second one of said cells.

27. The method of claim 25 wherein the step of applying heat uses application of laser energy exiting from the catheter in the form of a beam leaving said catheter with a width of less than 100 microns.

28. The method of claim 26 wherein the step of applying heat uses application of laser energy exiting from openings on a side of the catheter in the form of a plurality of beams, each leaving said catheter with a width of less than 100 microns, the plurality of beams causing porations in the cells, and said treatment agent is forced out said openings to follow multiple paths corresponding to said beams.

29. The method of claim 25 wherein the step of applying heat uses application of laser energy to heat an opaque portion of a part of the catheter in thermal transfer position relative to the patient such that the catheter in turn heats the cells.

30. The method of claim 25 wherein the step of applying heat uses the application of radio frequency energy to the cells.

31. The method of claim 25 wherein the step of applying heat uses application of microwave energy to the cells.

32. The method of claim 25 wherein the step of applying heat uses electrical heating of the cells.

33. The method of claim 25 wherein the step of applying heat uses chemically heating the cells.

34. The method of claim 25 wherein the step of applying heat uses heating the treatment agent prior to its insertion in the patient such that the treatment agent heats the cells.

* * * * *